United States Patent [19]

Küster et al.

[11] 4,281,186

[45] Jul. 28, 1981

[54] ACRYLYL AND METHACRYLYL UREAS CONTAINING QUATERNARY GROUPS, PROCESS FOR THEIR PREPARATION AND THEIR USE IN THE PREPARATION OF POLYMERS

[75] Inventors: Erich Küster, Krefeld; Kurt Dahmen, Monchen-Gladbach; Eduard Barthell, Krefeld, all of Fed. Rep. of Germany

[73] Assignee: Chemische Fabrik Stockhausen & Cie, Krefeld, Fed. Rep. of Germany

[21] Appl. No.: 104,989

[22] Filed: Dec. 18, 1979

[30] Foreign Application Priority Data

Dec. 27, 1978 [DE] Fed. Rep. of Germany ....... 2856384

[51] Int. Cl.$^3$ .............................................. C07C 127/22
[52] U.S. Cl. .................. 564/46; 260/32.6 R; 423/658.5
[58] Field of Search ...................... 260/553 E; 564/46

[56] References Cited

U.S. PATENT DOCUMENTS

| | | | |
|---|---|---|---|
| 3,551,159 | 12/1970 | Froehlich | 260/553 E X |
| 3,641,116 | 2/1972 | Froehlich | 260/553 E X |
| 3,919,091 | 11/1975 | Eckert et al. | 260/553 E X |
| 3,977,881 | 8/1976 | Kyburz et al. | 260/553 E X |
| 4,039,520 | 8/1977 | Habu et al. | 260/553 E X |
| 4,120,898 | 10/1978 | Smith et al. | 260/553 E X |

FOREIGN PATENT DOCUMENTS

| | | |
|---|---|---|
| 888316 | 8/1952 | Fed. Rep. of Germany . |
| 39-11973 | 6/1964 | Japan ..................... 260/553 E |

OTHER PUBLICATIONS

Wiley, J.A.C.S., 71, pp. 1310-1311, (1949).

Primary Examiner—Thomas A. Waltz
Attorney, Agent, or Firm—Sprung, Felfe, Horn, Lynch & Kramer

[57] ABSTRACT

The invention relates to acrylyl or methacrylyl ureas containing novel quaternary groups of the formula

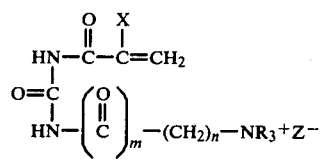

wherein
X is hydrogen or a methyl group,
R is a lower alkyl radical having from 1 to 4 carbon atoms,
m is 0 or 1,
n is an integer between 1 and 4, and
Z is a salt-forming anion.

The compounds are prepared from the corresponding halogen-substituted ureas by reaction with trialkylamines, preferably in a solvent. Because of their double bond, they can be polymerized to homopolymers and copolymers which are suited for use as flocculating, precipitating, dewatering and retention aids.

9 Claims, No Drawings

ACRYLYL AND METHACRYLYL UREAS CONTAINING QUATERNARY GROUPS, PROCESS FOR THEIR PREPARATION AND THEIR USE IN THE PREPARATION OF POLYMERS

The invention relates to acrylyl and methacrylyl ureas containing quaternary groups, to a process for their preparation, and to their use in the preparation of polymers.

Practically all cationic polymers and the monomers from which they are made derive their cationic characteristics from quaternary ammonium groups. (Bibliography: M. F. Hoover, J. Macromol. Sci. Chem. A [6] [1970], pp. 1327 to 1418.) Usually the tertiary amine, for example, 2-(dimethylamino)-ethylmethacrylate or N-(3-dimethylaminopropyl)acrylamide, is prepared first and then quaternized with a suitable reagent.

In contrast thereto, in the present invention a tertiary amine is alkylated with an olefinically unsaturated halogen compound directly to cationic monomers.

The invention thus provides ureas of the general formula

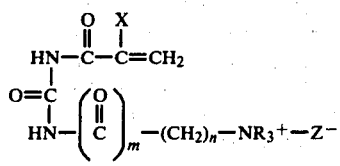

(I)

where X is either hydrogen or a methyl group, R is a lower alkyl radical having from 1 to 4 carbon atoms, m is either 0 or 1, n is an integer between 1 and 4, and Z is any salt-forming anion.

The compounds of formula (I) are obtained by reacting halogen-substituted ureas of the general formula

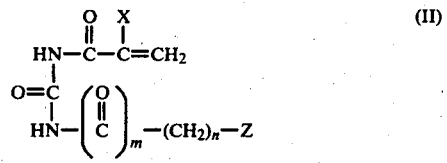

(II)

where X, m and n have the meaning given above and Z is a halogen, and in particular chlorine, bromine or iodine, with trialkylamines by known methods. (J. Goerdeler, in HoubenWeyl, Methoden der organischen Chemie [Methods of organic chemistry], 4th ed. [1958], vol. 11/2, p. 592 et seq. [Georg Thieme Verlag, Stuttgart].) Quaternization is usually carried out in a solvent. The preferred solvents are aliphatic and aromatic hydrocarbons, alcohols and/or ketones.

The reaction temperature generally ranges from about 20° to 100° C. It is determined primarily by the halogen substituent in the starting material. While the iodine compound will react even at room temperature, chlorine and bromine compounds require elevated temperatures, and it will then be advisable to employ pressures of up to 4 bars. The quaternary substances are obtained in solid form as a white powder which is readily soluble in water.

In accordance with a particularly preferred embodiment, the reaction is carried out at from 20° to 100° C. in acetone as solvent and with trimethylamine as the tertiary amine.

The anion is not limited to the class of halides. Other forms may readily be introduced through displacement reactions or ion exchange so that, for example, sulfates, perchlorates, nitrates or acetates, etc., are obtained.

The halogen-substituted ureas of formula (II) are prepared by the addition of isocyanates of the formula

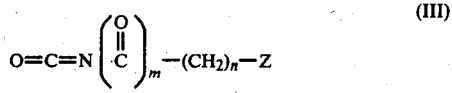

(III)

where m, n and Z have the meanings given above, to the α,β-unsaturated carboxylic acid amides of formula

(IV)

such as acrylamide or methacrylic acid amide. Suitable isocyanates are practically all halogen-substituted alkyl and acyl isocyanates, and particularly the ω-haloalkyl and acyl isocyanates, and more particularly 2-haloethyl b 3-halopropyl and 4-halobutyl isocyanate as well as 2-haloacetyl and 3-halopropionyl isocyanate.

There was no reason to believe at the outset that this reaction would prove successful. While the reaction of carboxylic acid amides with isocyanates has already been described (B. Kuhn, Ber. dtsch. chem. Ges. 17, 2880 [1884]; P. F. Wiley, J. Amer. Chem. Soc. 71, 1310 [1949]), and while acrylamide has already been reacted with aryl isocyanates according to German Pat. No. 888,316, that patent expressly states that a reaction with aliphatic isocyanates was not observed. It was therefore all the more surprising that this addition reaction should proceed smoothly.

The addition products are obtained simply by heating the two reactants with catalytic amounts of a tertiary amine. An aromatic hydrocarbon or a high-boiling ether is advantageously added as a diluent from which the ureas usually precipitate as crystals at the end of the reaction time.

The reaction with the haloalkyl isocyanates (m=0) is preferably carried out in aromatic hydrocarbons such as benzene, toluene or xylene at temperatures of up to 140° C., while in the case of the haloacyl isocyanates (m=1) high-boiling ethers such as 1,2-dimethoxyethane or tetrahydrofuran are preferably used as solvents, with the reaction then proceeding already at room temperature. Suitable tertiary amines are trialkylamines such as trimethylamine, triethylamine, tripropylamine, tributylamine, etc. Heterocyclic amines such as pyridine may also be used. However, trimethylamine is preferred.

Moreover, in view of the well-known propensity of acrylamides and methacrylamides for polymerizing, it is advisable to add a polymerization retarder such as hydroquinone, hydroquinone monomethylether, phenothiazine, etc.

The unsaturated urea compounds of formula (I) may be polymerized either alone or together with other polymerizable monomers. The term polymer is intended to include homopolymers, copolymers, terpolymers and other interpolymers.

The invention therefore also provides polymers derived from ureas, at least about 4% by weight comprising structural elements of the general formula (V):

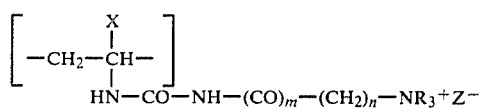

$$\left[ -CH_2-\overset{X}{\underset{|}{CH}}- \right] \quad (V)$$
$$HN-CO-NH-(CO)_m-(CH_2)_n-NR_3{}^+Z^-$$

where X, R, m, n and Z have the meanings given in formula (I). Suitable comonomers are all water-soluble, olefinically unsaturated compounds, for example, acrylic and methacrylic acid amides and their N-substituted derivatives, and in particular N-(3-dimethylaminopropyl)acrylamide and its salts and quaternary compounds, N-methylolacrylamide and methacrylamide and their ethers, amino-substituted acrylic and methacrylic acid esters such as diethylaminoethylacrylate and dimethylaminoethylmethacrylate, for example, and their salts and quaternary compounds, as well as vinyl esters such as vinyl acetate.

The polymerization is conducted conventionally; it may be initiated thermally, photochemically, by radiation, or with the usual radical initiators. It may be carried out in solution, suspension or emulsion. Suitable initiators are, for example, inorganic peroxides such as hydrogen peroxide; organic hydroperoxides and peroxides such as tert-butyl hydroperoxide, cumene hydroperoxide or dibenzoyl peroxide; aliphatic azo compounds decomposing into radicals, such as 2,2'-azobisisobutyronitrile; redox catalyst systems such as persulfate or chlorate with disulfite or iron(II) salts; and also transition-metal chelates which are known radical formers. The initiators are generally used in an amount of from 0.001 to 1 weight percent, based on the amount of monomer. The optimum amount and the most effective initiator can readily be determined by experimentation.

The polymerization is advantageously conducted in the presence of a solvent or diluent. The suspension, solution or emulsion polymerization processes used with other monomers may be used also for the polymers in accordance with the invention. Optionally such auxiliaries as buffers, dispersants, protective colloids and the like may be used. The polymers in accordance with the invention may be used as flocculants, precipitants, dewatering and retention agents. They are characterized by solubility in water. Moreover, these aqueous solutions have but low viscosity, which is highly advantageous for their use. Because of the presence of the very stable urea groupings in the polymers, they also have excellent hydrolytic stability.

The examples which follow will serve to illustrate the invention.

(A) PREPARATION OF UREAS OF FORMULA (I):

EXAMPLE 1

N-acrylyl-N'-(2-chloroethyl)urea

A mixture of 71.1 g (1.0 mole) acrylamide, 0.5 g triethylamine, 0.5 g 2,6-ditert-butyl-4-methylphenol and 50 ml benzene is mixed with 110.8 g (1.05 mole) 2-chloroethyl isocyanate and heated in an autoclave over a period of 10 hours to 110° C. The finely crystalline precipitate obtained on cooling is filtered off. 140 g of substance is so obtained. It is recrystallized from 700 ml acetonitrile to yield 115 g (0.65 mole=65% of theory) white crystal needles having a melting point between 156° and 158° C.

| $C_6H_9ClN_2O_2$ | Cl calc. 20.07 | N calc. 15.86 |
|---|---|---|
| 176.60 | found 19.80 | found 15.90 |

$^1$H NMR spectrum (in CDCl$_3$): δ=3.5 to 3.8 (m,4); 5.7 to 6.8 (m,3); 9.05 (m,1); 10.4 (m,1)

EXAMPLE 2

N-acrylyl-N'-(2-bromoethyl)urea

By the procedure of Example 1, there is obtained from 165 g (1.1 mole) 2-bromoethyl isocyanate after 10 hours at 110° C. 184 g of crude product, which after recrystallization from 600 ml acetonitrile yields 104 g (0.7 mole=70% of theory) white crystal needles having a melting point between 157° and 159° C.

| $C_6H_9BrN_2O_2$ | Br calc. 36.15 | N calc. 12.67 |
|---|---|---|
| 221.06 | found 35.90 | found 12.90 |

$^1$H NMR spectrum (in CDCl$_3$): δ=3.3 to 4.0 (m,4); 5.7 to 6.8 (m,3); 9.0 (m,1); 10.2 (m,1)

EXAMPLE 3

N-acrylyl-N'-(3-chloropropyl)urea

By the procedure of Example 1, there is obtained from 131.6 g (1.1 mole) 3-chloropropyl isocyanate after 16 hours at 110° C. 130 g of crude product, which after recrystallization from 400 ml acetonitrile yields 86 g (0.45 mole=45% of theory) white crystal needles having a melting point between 105° and 107° C.

| $C_7H_{11}ClN_2O_2$ | Cl calc. 18.60 | N calc. 14.70 |
|---|---|---|
| 190.63 | found 18.33 | found 14.49 |

$^1$H NMR spectrum (in CDCl$_3$): δ=1.75 to 2.3 (m,2); 3.25 to 3.8 (m,4); 5.7 to 6.8 (m,3); 8.8 (m,1); 10.55 (m,1)

EXAMPLE 4

N-(2-chloroethyl)-N'-methacrylylurea

By the procedure of Example 1, there is obtained from 85.1 g (1.0 mole) methacrylamide and 110.8 g (1.05 mole) 2-chloroethyl isocyanate after 10 hours at 110° C. 140 g of crude product, which after recrystallization from 350 ml acetonitrile yields 105 g (0.55 mole=55% of theory) white crystal needles having a melting point between 122° and 123° C.

| $C_7H_{11}ClN_2O_2$ | Cl calc. 18.60 | N calc. 14.70 |
|---|---|---|
| 190.63 | found 18.73 | found 14.78 |

$^1$H NMR spectrum (in CDCl$_3$): δ=2.05 (d,3); 3.7 (d,4); 5.5 to 6.2 (m,2); 9.0 (m,1); 9.5 (m,1)

EXAMPLE 5

N-acrylyl-N'-(2-chloroacetyl)urea

To a solution of 71.1 g (1.0 mole) acrylamide in 150 ml 1,2-dimethoxyethane there is added dropwise 125.5 g (1.05 mole) 2-chloroacetyl isocyanate at between 25° and 30° C., followed by 24 hours' agitation. Filtration yields 140 g of crude product, which is recrystallized from 540 ml acetonitrile. 106 g (0.56 mole=56% of theory) white crystals having a melting point between 144° and 145° C. is obtained.

| $C_6H_7ClN_2O_3$ | Cl calc. 18.60 | N calc. 14.70 |
|---|---|---|
| 190.59 | found 18.70 | found 14.90 |

$^1$H NMR spectrum (in d$_6$-DMSO): δ=4.65 (s,2); 5.8 to 6.7 (m,3); 11.1; 11.35 (M,1)

(B) PREPARATION OF UREAS OF FORMULA (I):

EXAMPLE 6

Acrylylureylene ethylene trimethylammonium chloride 35.3 g (0.2 mole) N-acrylyl-N'-(2-chloroethyl)urea is cooled with 0.2 g 2,6-ditert-butyl-4-methylphenol in 400 ml acetone to 0° C. and 23.6 g (0.4 mole) liquid trimethylamine is then added. The mixture is heated in an autoclave over a period of 20 hours to 80° C. and then cooled, and the precipitate is filtered. After washing with acetone and ether, 33 g (0.14 mole=70% of theory) white crystal powder is obtained.

| $C_9H_{18}ClN_3O_2$ | Cl calc. 15.04 | N calc. 17.83 |
|---|---|---|
| 235.71 | found 14.90 | found 17.12 |

$^1$H NMR spectrum (in D$_2$O): δ=3.25 (s,9); 3.5 to 4.0 (m,4); 5.8 to 6.5 (m,3)

EXAMPLE 7

Methacrylylureylene ethylene trimethylammonium chloride

By the procedure of Example 6, there is obtained from 38.1 g (0.2 mole) N-(2-chloroethyl)-N'-methacrylylurea 34 g (0.14 mole=68% of theory) white crystal powder.

| $C_{10}H_{20}ClN_3O_2$ | Cl calc. 14.20 | N calc. 16.83 |
|---|---|---|
| 249.74 | found 14.56 | found 16.76 |

$^1$H NMR spectrum (in D$_2$O): δ=1.95 (d,3); 3.2 (s,9); 3.5 to 4.0 (m,4); 5.6 to 5.9 (m,2)

EXAMPLE 8

Acrylylureylene propylene trimethylammonium chloride

By the procedure of Example 6, there is obtained from 38.1 g (0.2 mole) N-acrylyl-N'-(3-chloropropyl)urea 47 g (0.19 mole=94% of theory) white crystal powder containing some acetone of crystallization.

| $C_{10}H_{20}ClN_3O_2$ | Cl calc. 14.20 | N calc. 16.83 |
|---|---|---|
| 249.74 | found 12.87 | found 14.59 |

$^1$H NMR spectrum (in D$_2$O): δ=1.7 to 2.4 (m,2); 3.15 (s,9); 3.1 to 3.8 (m,4); 5.8 to 6.7 (m,3)

EXAMPLE 9

Acrylylureylene ethylene trimethylammonium iodide 26.8 g (0.1 mole) N-acrylyl-N'-(2-iodoethyl) urea is cooled with 0.2 g 2,6-ditert-butyl-4-methylphenol in 300 ml acetone to 0° C. and 11.8 g (0.2 mole) liquid trimethylamine is added. The mixture is agitated for 24 hours and the precipitate is filtered off. After washing with acetone and ether, 30 g (0.092 mole=92% of theory) white crystal powder is obtained.

| $C_9H_{18}IN_3O_2$ | I calc. 38.79 | N calc. 12.84 |
|---|---|---|
| 327.17 | found 39.24 | found 12.55 |

$^1$H NMR spectrum (in D$_2$O): δ=3.3 (s,9); 3.6 to 4.0 (m,4); 5.9 to 6.7 (m,3)

(C) PREPARATION AND USE OF POLYMERS OF FORMULA (V):

EXAMPLES 10 TO 14

Copolymers of acrylamide and monomers in accordance with the invention (General directions.)

The acrylamide and the cationic monomer are dissolved in water and the temperature of the solution is adjusted to 15° C. and the pH value to 3.0. The solution is purged of oxygen by the injection of nitrogen (1 hour). The amounts of 2,2'-azobisisobutyronitrile (AIBN), potassium peroxydisulfate, and sodium dithionite and iron(II) sulfate specified in Table 1 are used as catalyst, polymerization thus being initiated promptly. The maximum temperature is reached after some 30 to 60 minutes. After cooling, the colorless gel obtained is comminuted and dewatered with from 2 to 3 liters methanol. After filtration, adhering methanol is drawn off in a vacuum. The yield is about quantitative.

TABLE 1

| Example | ACA (g) | Amount (g) | According to example | Water (g) | Active substance % | QUAT CATALYST AiBN (mg) | $K_2S_2O_8$ (mg) | $Na_2S_2O_4$/ $FeSO_4$ (mg) | Temp. (°C.) | Viscosity of 1% sol. (mPa/sec) | Mol. wgt. determined viscosimetrically |
|---|---|---|---|---|---|---|---|---|---|---|---|
| 10 | 90 | 10 | 6 | 300 | 25 | 5 | 3 | 10/2 | 80 | 920 | $2.2 \times 10^6$ |
| 11 | 70 | 30 | 6 | 300 | 25 | 10 | 6 | 20/4 | 70 | 720 | $1.6 \times 10^6$ |
| 12 | 90 | 10 | 7 | 300 | 25 | 5 | 3 | 10/2 | 78 | 2000 | $2.7 \times 10^6$ |
| 13 | 70 | 30 | 7 | 300 | 25 | 10 | 4 | 15/2 | 77 | 1040 | $1.5 \times 10^6$ |
| 14 | 180 | 20 | 9 | 600 | 25 | 10 | 5 | 15/2 | 70 | 500 | $1.8 \times 10^6$ |

EXAMPLE 15

The suitability of the polymers in accordance with the invention as dewatering agents for sewage sludges is demonstrated by the two tests summarized below. The dewatering times were determined by the CST (Capillary Suction Time) method.

TABLE 2

| Example | Viscosity of 1% solution in distilled water. (mPa/sec) | Capillary flow time with addition of an 0.1% solution to Krefeld tap water (sec) | | | | |
|---|---|---|---|---|---|---|
| | | Addition | 80 | 100 | 125 | 150 ppm |
| 10 | 920 | | 71 | 45 | — | 21 |
| 11 | 720 | | — | 50 | 40 | 11 |

TABLE 2-continued

| Example | Viscosity of 1% solution in distilled water. (mPa/sec) | Capillary flow time with addition of an 0.1% solution to Krefeld tap water (sec) | | |
|---|---|---|---|---|
| Product based on DMAEMA*/CH$_3$Cl | 9000 | — | — | 47 | 30 |

| | | Addition | 100 | 150 | 200 | ppm |
|---|---|---|---|---|---|---|
| 12 | 2000 | | 127 | 53 | 33 | |
| 13 | 1040 | | 74 | 32 | 14 | |
| Product based on DMAEMA*/CH$_3$Cl | 9000 | | 200 | 63 | 22 | |

*2-Dimethylaminoethylmethacrylate.

Despite the low viscosity of the aqueous solutions, consistently better results are obtained with the products in accordance with the invention than with the copolymers based on DMAEMA/CH$_3$Cl used up to now.

Literature:

(1) R. Baskerville and R. Gale: "A simple automatic instrument for determining the filtrability of sewage sludges." (Water Pollution Control 67 [1968], 233-241.)

(2) R. Gale and R. Baskerville: "Capillary suction method for determination of the filtration properties of a solid/liquid suspension." (Chemistry & Industry [1967], 355-356.)

EXAMPLE 16

The suitability of the products for use as dewatering and retention aids in papermaking is illustrated by the tests summarized below, performed on standardized pulp suspensions.

| Paper pulp: | 60% spruce sulfite |
| | 40% hardwood pulp |
| Filler: | 30% SPS clay |
| Degree of fineness: | 38° SR |
| Dosage of aid: | 0.02%, based on pulp |

For evaluation of the effectiveness of the products, the dewatering times and the retention effect were determined in a Schopper-Riegler fineness testing apparatus. The results are presented in Table 3.

TABLE 3

| Product | Dewatering time (sec) | Retention (%) |
|---|---|---|
| Control | 25 | 72 |
| Example 10 | 21 | 90 |
| Example 11 | 18 | 89 |
| Copolymer based on DMAEMA/CH$_3$/Cl | 29 | 91 |

The products prepared in accordance with the invention were found to be effective under the test conditions, which substantially corresponded to those used in paper technology. Since the products are also highly fluid in aqueous solution and therefore easy to handle, that is to say, readily dosable and readily soluble, they lend themselves well to use in papermaking.

EXAMPLE 17

The products prepared in accordance with the invention were tested as precipitants in flocculation tests. Their flocculating behavior in an aqueous solution was determined after they had been added to aqueous clay suspensions, prepared by making kaolin into a slurry and adjusted with an aluminum sulfate solution to a pH of about 4.8. The results are presented in Table 4.

TABLE 4

| Flocculating effect on a clay pulp with 20 g/l solids content | | |
|---|---|---|
| Product | Amount added (ppm) | Time (sec) |
| Control | | 180 |
| Example 10 | 4 | 4.7 |
| Example 11 | 4 | 14.0 |
| Example 12 | 4 | 6.9 |
| Example 13 | 4 | 18.6 |
| Example 14 | 4 | 5.4 |

Literature:

H. Akyel and M. Neven, Chemie-Ing. Technik 39 (1967), 172.

It will be appreciated that the instant specification and examples are set forth by way of illustration and not limitation, and that various modifications and changes may be made without departing from the spirit and scope of the present invention.

What is claimed is:

1. A urea of the formula

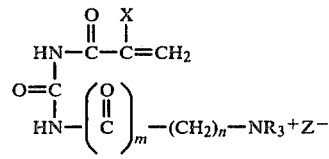

wherein

X is hydrogen or a methyl group,

R is a lower alkyl radical having from 1 to 4 carbon atoms, m is 0 or 1, n is an integer between 1 and 4, and Z is a salt-forming anion.

2. A urea according to claim 1, wherein

R is ethyl, n is 1 or 2, and

Z is chlorine.

3. A urea according to claim 1, wherein

R is methyl n is 1 or 2, and

Z is chlorine.

4. A process for the preparation of a urea according to claim 1, wherein Z is halogen and m is 0, comprising reacting a haloalkyl or haloacyl isocyanate of the formula

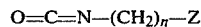

with an α,β-unsaturated carboxylic acid amide of the formula

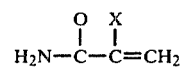

to produce a halogen-substituted urea of the formula

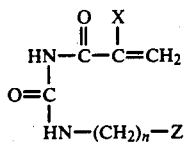

and reacting the halogen-substituted urea in a solvent with a trialkylamine of the formula $NR_3$ at a temperature from about 20° to 100° C. and at a pressure from about 1 to 4 bars.

5. A process according to claim 4, wherein the reaction of the isocyanate with the carboxylic acid amide is carried out at a temperature from about 20° to 140° C. and at a pressure from about 1 to 4 bars in the presence of a solvent and of a tertiary amine as catalyst.

6. A process according to claim 4, wherein the reaction of the isocyanate with the carboxylic acid amide is carried out in an aromatic hydrocarbon or high-boiling ether as solvent.

7. A process according to claim 4, wherein the trialkylamine is trimethylamine.

8. A process according to claim 4, wherein the halogen-substituted urea is reacted with the trialkylamine in the presence of a hydrocarbon, alcohol or ketone as solvent.

9. A process according to claim 5, wherein n is 2 the reaction of the isocyanate with the carboxylic acid amide is carried out in an aromatic hydrocarbon or high-boiling ether as solvent, the trialkylamine is trimethylamine and the halogen-substituted urea is reacted with the trimethylamine in the presence of a hydrocarbon, alcohol or ketone as solvent.

* * * * *